US00PP32278P2

(12) United States Plant Patent
Landin Outón

(10) Patent No.: US PP32,278 P2
(45) Date of Patent: Oct. 6, 2020

(54) ***ILEX* PLANT NAMED 'LAND GREEN'**

(50) Latin Name: *Ilex crenata*
Varietal Denomination: Land Green

(71) Applicant: José Luis Landin Outón, Pontevedra (ES)

(72) Inventor: José Luis Landin Outón, Pontevedra (ES)

(73) Assignee: VAN VLIET NEW PLANTS B.V., Stroe (NL)

( * ) Notice: Subject to any disclaimer, the term of this patent is extended or adjusted under 35 U.S.C. 154(b) by 0 days.

(21) Appl. No.: 16/602,443

(22) Filed: Oct. 4, 2019

(30) Foreign Application Priority Data

Jul. 17, 2019 (QZ) ..... PBR 2019/1745

(51) Int. Cl.
*A01H 5/12* (2018.01)
*A01H 6/00* (2018.01)

(52) U.S. Cl.
USPC ..... Plt./247

(58) Field of Classification Search
USPC ..... Plt./247
CPC ..... A01H 6/00; A01H 5/00; A01H 5/12
See application file for complete search history.

*Primary Examiner* — Keith O. Robinson
(74) *Attorney, Agent, or Firm* — Penny J. Aguirre

(57) ABSTRACT

A new cultivar of *Ilex crenata* plant named 'Land Green' that is characterized by its pyramidal plant shape that requires little pruning to maintain a pyrimidal shape, its leaves that are dark green in color and its compact plant habit.

2 Drawing Sheets

Botanical classification: *Ilex crenata.*
Variety denomination: 'Land Green'.

CROSS REFERENCE TO A RELATED APPLICATION

This application is related to a European plant breeders' rights application filed on Jul. 17, 2019, application No. 2019/1745. There have been no offers for sale anywhere in the world more than one year prior to the filing of this Application and no accessibility to one of ordinary skill in the art could have been derived from the printed plant breeder's rights documents.

BACKGROUND OF THE INVENTION

The present invention relates to a new and distinct cultivar of *Ilex crenata* and will be referred to hereafter by its cultivar name, 'Land Green'. 'Land Green' is a new cultivar of Japanese holly grown for use as an ornamental landscape plant.

'Land Green' was discovered by the Inventor as a chance seedling in a trial field in Pontevedra, Spain in June of 2009. The parentage is unknown as there were numerous cultivars of *Ilex crenata* growing in the field including 'Fastigiate', 'Golden Gem', 'Green Gem', and 'Stokes' (all unpatented).

Asexual propagation of the new cultivar was first accomplished by one of the Inventors using softwood stem cuttings in July of 2014 in Pontevedra, Spain. Asexual propagation by softwood stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'Land Green' as a unique cultivar of *Ilex.*

1. 'Land Green' exhibits a pyramidal plant shape that requires little pruning to maintain a pyrimidal shape.
2. 'Land Green' exhibits leaves that are dark green in color.
3. 'Land Green' exhibits a compact plant habit.

'Land Green' can be most closely compared to the *Ilex crenata* cultivars 'Convexa' (not patented) and 'Stokes' (not patented). 'Convexa' is similar to 'Land Green' in having dark green foliage. 'Convexa' differs from 'Land Green' in having a less pyramidal plant shape, a less compact plant habit, leaves that are more convexed in aspect, and in requiring more pruning to maintain a pyrimidal shape. 'Stokes' is similar to 'Land Green' in leaf shape. 'Stokes' differs from 'Land Green' in having a less pyramidal plant shape, a less compact plant habit, and a more vigorous growth rate.

BRIEF DESCRIPTION OF THE DRAWINGS

The accompanying colored photographs illustrate the overall appearance and distinct characteristics of a six-month-old plant of the new cultivar as grown outdoors in a 9-cm container (planted with 2 plugs) in Boskoop, The Netherlands.

The photograph in FIG. 1 provides a side view of the plant habit of 'Land Green'.

Figure 1:
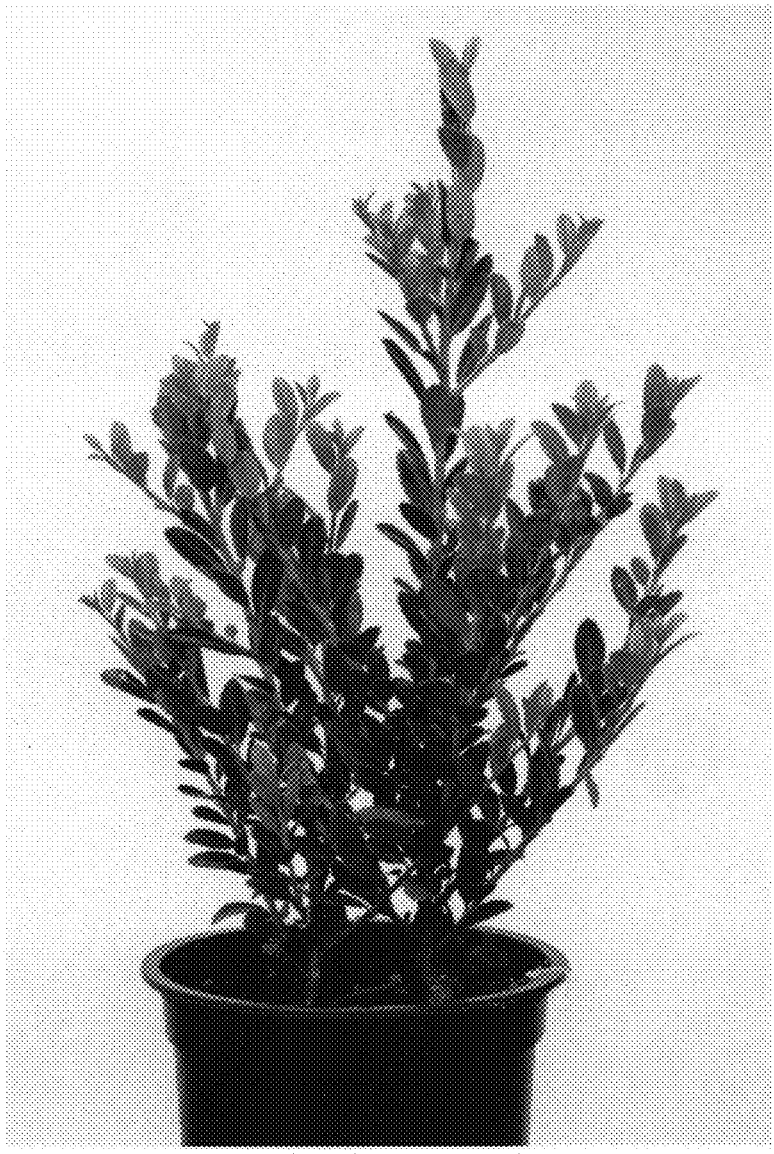
Figure 2:
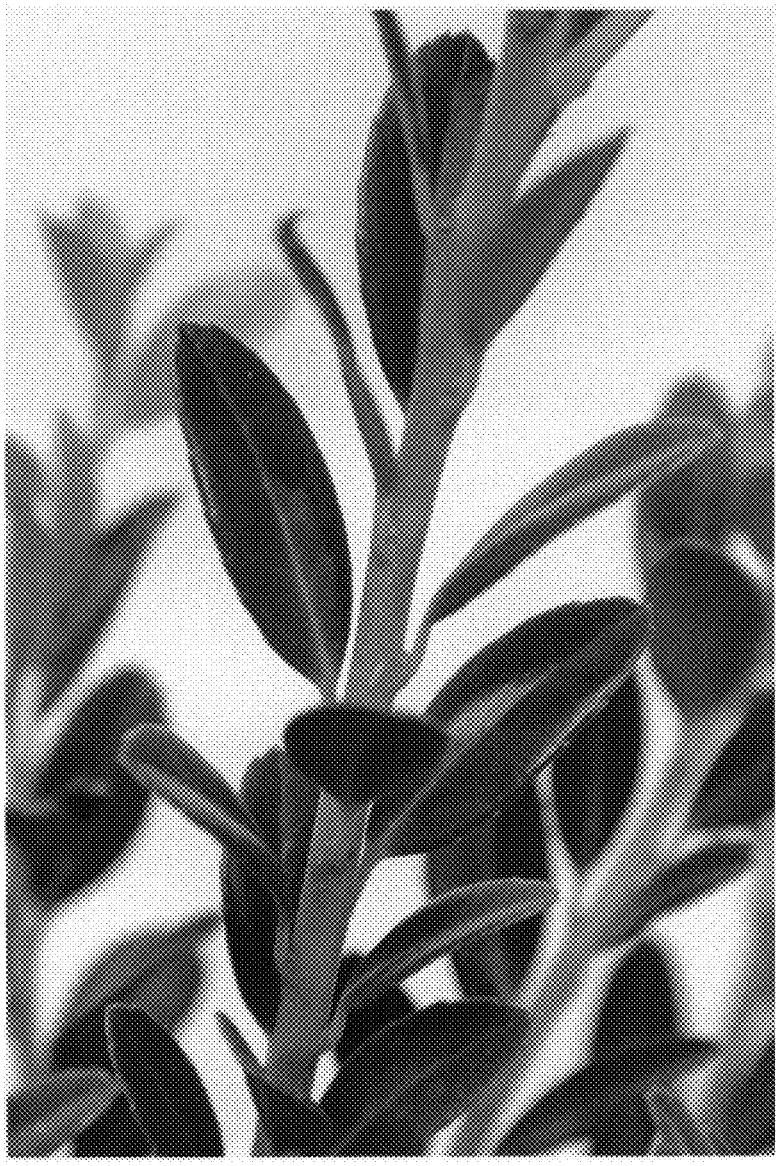

The photograph in FIG. 2 provides a close-up view of the foliage of 'Land Green'.

The colors in the photographs may differ slightly from the color values cited in the detailed botanical description, which accurately describe the colors of the new *Ilex.*

DETAILED BOTANICAL DESCRIPTION

The following is a detailed description of six-month-old plants of the new cultivar grown in a conventional greenhouse in 9-cm containers (planted with 2 plugs) in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen, perennial shrub.

*Plant habit*.—Pyramidal, upright.

*Height and spread*.—Reaches an average of 20.1 cm in height and 11.5 cm in width, as a mature plant in the landscape plant reaches an average of 100 cm in height and 40 cm in width.

*Hardiness*.—At least to U.S.D.A Zones 6 to 10.

*Diseases and pests*.—No susceptibility to diseases has been observed.

*Root description*.—Densely fibrous and 165C in color.

*Propagation*.—Softwood stem cuttings.

*Root development*.—An average of 12 weeks for root initiation and 8 months to produce a young rooted plant.

*Growth rate*.—Moderate.

Branch description:

*Branching*.—Freely branching; 1 main branch each with an average of 12 lateral branches.

*Stem size*.—An average of 10.1 cm in height and 2 mm in diameter.

*Stem surface*.—Both surfaces slightly glossy and moderately covered with very small glands, 144C in color.

*Stem shape*.—Rounded.

*Stem aspect*.—Lateral branches an average angle of 42.5° to main branches.

*Stem strength*.—Strong.

*Stem color*.—Young stems; 144B, mature stems; 143C, older stems; 197A to 197B.

*Internode length*.—Average of 4 mm.

Foliage description:

*Leaf shape*.—Elliptic to oblong.

*Leaf division*.—Simple.

*Leaf base*.—Acute.

*Leaf apex*.—Bluntly acute.

*Leaf fragrance*.—None.

*Leaf venation*.—Pinnate, upper surface veins 143B, lower surface veins 144A to 144B.

*Leaf margins*.—Entire, upper half of leaves with a crenate margin.

*Leaf arrangement*.—Alternate.

*Leaf aspect*.—Very slightly convexed, slightly carinate.

*Leaf attachment*.—Petiolate.

*Leaf surface*.—Both surfaces smooth and glabrous, upper surface glossy, lower surface matte with numerous glands present; an average of 60 per leaf, 0.1 mm in diameter that match leaf color.

*Leaf size*.—Average of 1.8 cm in length and 8 mm in width.

*Leaf quantity*.—Average of 26 per lateral branch.

*Leaf color*.—Young leaves upper surface; 143B to 143C, young leaves lower surface; 144C, mature upper surface; a color between NN137A and 147A, mature lower surface; 138A.

*Petioles*.—Average of 3 mm in length and 7.5 mm in diameter, strong, smooth and glabrous surface, 144B to 144C in color.

Flower description: None produced to date.

It is claimed:

1. A new and distinct cultivar of *Ilex* plant named 'Land Green' as herein illustrated and described.

* * * * *